United States Patent [19]

Itoh et al.

[11] Patent Number: 4,948,659

[45] Date of Patent: Aug. 14, 1990

[54] PROCESS FOR PREPARATION OF WATER ABSORPTIVE COMPOSITE

[75] Inventors: Kiichi Itoh; Takeshi Shibano, both of Yokkaichi, Japan

[73] Assignees: Mitsubishi Petrochemical Company Limited, Tokyo; Uni-Charm Corporation, Kawanoe, both of Japan

[21] Appl. No.: 267,277

[22] Filed: Nov. 4, 1988

[30] Foreign Application Priority Data

Nov. 6, 1987 [JP] Japan ................................ 62-280339

[51] Int. Cl.$^5$ ............................ B32B 7/00; D04B 1/00
[52] U.S. Cl. .................................... 428/254; 428/260; 428/264; 428/265; 428/290; 428/913; 427/342; 427/389.9; 427/391; 427/392
[58] Field of Search ...................... 427/342, 389.9, 391, 427/392; 428/264, 265, 290, 254, 260, 913; 524/733, 760, 812, 817, 833

[56] References Cited

U.S. PATENT DOCUMENTS

| | | | |
|---|---|---|---|
| 4,295,987 | 10/1981 | Parks | 428/264 X |
| 4,455,342 | 6/1984 | Fink et al. | 427/389.9 X |
| 4,605,401 | 8/1986 | Chmelir et al. | 428/264 X |
| 4,748,076 | 5/1988 | Saotome | 427/389.9 X |

Primary Examiner—Michael Lusignan
Attorney, Agent, or Firm—Oblon, Spivak, McClelland, Maier & Neustadt

[57] ABSTRACT

There is provided a process for preparing a water absorptive composite, which comprises the combination of the steps of (A) applying an aqueous solution containing (a) a polymerizable monomer comprising as a main component acrylic acid, of which 20% or more of the carboxyl groups have been neutralized to its alkali metal salt or ammonium salt, (b) a crosslinking agent, (c) a polyoxyethylene acyl ester with HLB of 7 or more and (d) an oxidative radical polymerization initiator to a prefabricated fibrous substrate and (B) polymerizing the polymerizable monomer applied to the fibrous substrate with addition of a reducing agent to form a composite of a polymer derived from the polymerizable monomer and the fibrous substrate.

19 Claims, No Drawings

PROCESS FOR PREPARATION OF WATER ABSORPTIVE COMPOSITE

BACKGROUND OF THE INVENTION

1. Field of the Art

This invention relates to a process for preparing a water absorptive composite comprising a water absorptive polymer and a prefabricated fibrous substrate. More particularly, this invention relates to a process for preparing a water absorptive composite in which a highly water absorptive polymer is held on a prefabricated substrate, comprising applying an aqueous solution containing an acrylic acid type monomer, a polyoxyethylene acyl ester with HLB of 7 or more, a cross-linking agent and an oxidative radical polymerization initiator to a prefabricated fibrous substrate, and then carrying out polymerization at room temperature within a short time with addition of a reducing agent.

The water absorptive composite obtained by the process according to this invention can be advantageously used in the production of a variety of water absorptive materials, because it has a remarkably high water absorption rate and an extremely low content of unpolymerized monomers, and the highly water absorptive polymer is held with good stability on the fibrous substrate.

2. Prior Art

Materials such as paper, pulp, nonwoven fabric, spongy urethane resins and the like have hitherto been used as water retentive materials for a variety of sanitary goods such as a sanitary napkin, paper diaper and the like and a variety of agricultural materials. However, these materials have a water absorption capacity of no more than 10-50 times their own weight, which will cause problems that an extensively increased bulk of the material is required for absorbing or retaining a large amount of water and that water is easily released from the material in which water has been absorbed on pressing it.

There have recently been proposed a variety of highly water absorptive polymer materials in order to settle the aforementioned problems of the water absorptive materials of this kind. For instance, there have been proposed a graft polymer of starch (Japanese Patent Publication No. 46199/78, etc.), a denaturated cellulose (Unexamined Published Japanese Patent Application No. 80376/75, etc.), a crosslinked water soluble polymer (Japanese Patent Publication No. 23462/68, etc.), a self-crosslinking polymer of an alkali metal salt of acrylic acid (Japanese Patent Publication No. 30710/79, etc.), and the like.

However, these highly water absorptive polymer materials, while having a relatively high level of water absorption properties, are obtained as powder in most cases. Therefore, in order to use them for sanitary goods such as a sanitary napkin, paper diaper or the like, it is necessary to disperse them homogeneously on such substrates as tissue paper, nonwoven fabric, cotton or the like. However, the polymer powder having been dispersed in such a manner is difficult to be firmly held on the substrate and often agglomerate partially. Also, swollen gel after water absorption will easily move from the substrate without being held firmly on it. Therefore, if it is used for a paper diaper, for example, it will give the feeling of stiffness upon urination accompanied with the extremely uncomfortable feeling on wearing. Furthermore, in a process for obtaining an absorber by dispersing such a powdery polymer as described above on a substrate, the absorber will be very expensive because of complicated procedures for powder handling and of problems on processes for efficiently conducting uniform dispersion.

As a method for dissolving these problems, there is disclosed a process for producing a water absorptive composite in which an aqueous solution of an acrylic acid type monomer is applied in a previously determined pattern to a prefabricated fibrous substrate to obtain a composite, which is then irradiated with electromagnetic radiation or corpuscular ionizing radiation to convert the acrylic acid type monomer into a highly water absorptive polymer (Unexamined Japanese PCT Patent Publication No. 500546/82). According to this process, uniform dispersion and stable holding of the aforementioned powder on a substrate are considerably improved. However, since electromagnetic radiation or corpuscular ionizing radiation is employed for converting the monomer into the high water absorptive polymer in this process, the highly water absorptive polymer inherent to the specific monomer tends to be cross-linked excessively. As the result, the composite obtained will exhibit extremely poor properties as an absorber. Especially its water absorption capacity will be of a level of only half or less of that of the composite obtained by using the aforementioned highly water absorptive powdery polymer. Moreover, this process involves problems in respect of safety on operation of a device for the above radiation and also production cost.

More recently, Unexamined Published Japanese Patent Application No. 149609/85 discloses a process for preparing a water absorptive composite material comprising previously impregnating a water absorptive organic material with an aqueous solution of an acrylic acid type monomer and adding thereto in a mist form a water soluble radical polymerization initiator, or, a water soluble radical polymerization initiator and a water soluble reducing agent to conduct polymerization. In this process, however, the water soluble polymerization initiator is added after the water absorptive organic material has been impregnated with the acrylic acid type monomer. Thus, although the polymerization initiator is added in a mist form, it is very difficult to completely polymerize the monomer because of occurrence of "uneven polymerization" and as the result the amount of the residual monomers is in a high level, which will cause problems on safety and lead to lowering of the properties of the resulting product, especially in respect of its water absorption capacity.

Under these backgrounds, the present inventors have already proposed in Japanese Patent Application No. 238421/85 a method that an aqueous solution of an acrylic acid type monomer containing a small amount of a crosslinking agent and an oxidative radical polymerization initiator are previously mixed and the mixture is applied to a fibrous substrate, and then an amine or a reducing agent is added to conduct polymerization. It has been found that according to this method there hardly occurs "uneven polymerization", polymerization proceeds very easily and a composite having a large water absorption capacity can be obtained. The water absorptive composite produced by this method is, however, still insufficient in its water absorption rate. Thus a method has been sought for which can provide a water absorptive composite having enhanced water absorption rate.

SUMMARY OF THE INVENTION

This invention is directed to an improvement of the processes for producing a water absorptive composite described in the above mentioned Japanese Patent Application No. 238421/85, Unexamined Japanese PCT Patent Publication No. 500546/82 and Unexamined Published Japanese Patent Application No. 149609/85, providing a process for preparing very easily under a moderate condition a water absorptive composite which has no remaining monomers and excellent water absorption properties, especially, a remarkably high water absorption rate.

The present inventors have conducted an intensive research in order to solve the aforementioned problems. As the result, they have found that a water absorptive composite which contains very few remaining monomers, is very excellent in water absorption properties and in which the highly water absorptive polymer is held with good stability on the fibrous substrate, can be obtained very easily in a very short time of polymerization by applying an aqueous solution containing an acrylic acid type monomer, a polyoxyethylene acyl ester with HLB of 7 or more, a crosslinking agent and an oxidative radical polymerization initiator to a prefabricated substrate and then adding a reducing agent in a mist form, and finally reached the present invention.

Thus, the process for producing a water absorptive composite according to the present invention comprises the combination of the steps of (A) applying an aqueous solution containing (a) a polymerizable monomer comprising as a main component acrylic acid, of which 20% or more of the carboxyl groups have been neutralized to its alkali metal salt or ammonium salt, (b) a crosslinking agent, (c) a polyoxyethylene acyl ester with HLB of 7 or more and (d) an oxidative radical polymerization initiator to a prefabricated fibrous substrate and (B) polymerizing the polymerizable monomer applied to the fibrous substrate with addition of a reducing agent to form a composite of a polymer derived from the polymerizable monomer and the fibrous substrate.

The process for preparing a water absorptive composite according to the present invention has marked characteristics in the following points:

(a) Coexistence of a polyoxyethylene acyl ester having HLB of 7 or more with an acrylic acid type monomer provides a polymer having a very high water absorption rate.

(b) There is adopted a manner that an oxidative radical polymerization initiator is previously dissolved in an aqueous solution of the polyoxyethylene acyl ester and the acrylic acid type monomer, and a reducing agent is sprayed thereto thereby commencing polymerization, which manner drastically reduces the amount of remaining monomers, makes polymerization operation simple and enables to conduct polymerization under mild conditions as at about room temperature within a very short period of time.

Thus, the water absorptive composite obtained according to the instant process has a remarkably high water absorption rate, contains very few remaining monomers and thus is very safe in practical use as compared with those produced by the processes disclosed in the aforementioned Japanese Patent Application No. 238421/85, Unexamined Japanese PCT Patent Publication No. 500546/82 and Unexamined Published Patent Application No. 149609/85, as apparent from Examples and Comparative Examples set forth below. Further, the composite handles easily because of its sheet form as compared with conventional powdery water absorptive resins, so that they can be used advantageously for the production of a variety of sanitary goods such as a sanitary napkin, paper diaper and the like.

The water absorptive composite according to the present invention, taking advantage of its excellent water absorption capacity and easy handling, can be also used for the production of a variety of materials for gardening and agriculture such as a soil conditioner and a water retaining agent which have recently attracted public attention.

DETAILED DESCRIPTION OF THE INVENTION

Step (A)

Polymerizable Monomer

The polymerizable monomer used in the present invention comprises as a main component acrylic acid, of which 20% or more, preferably 50% or more of the carboxyl groups are neutralized into its alkali metal salt or ammonium salt. If the partial neutralization degree is less than 20%, the water absorption capacity of the resulting polymer will be remarkably lowered.

According to the present invention, it is possible to use, in addition to the acrylic acid type monomer, one or more kinds of second monomers as far as the use thereof does not impair the water absorption properties of the resulting polymer. Examples of the second monomers may include (a) methacrylic acid, itaconic acid, maleic acid, fumaric acid, 2-acrylamide-2-methylpropanesulfonic acid, 2-acryloylethanesulfonic acid, 2-acryloylpropanesulfonic acid and the salts thereof, (b) vinylpyridines such as 2-vinylpyridine and 4-vinylpyridine and the salts thereof, (c) alkyl or alkoxy esters of dicarboxylic acids such as itaconic acid, maleic acid and fumaric acid, (d) vinylsulfonic acid, (e) methyl acrylate, ethyl acrylate, etc., (f) hydroxyethyl (meth)acrylate, hydroxypropyl (meth)acrylate, and (g) polyethylene glycol mono(meth)acrylate.

For neutralization of the acrylic acid type monomer or the aforementioned acid monomers may be used a hydroxide or bicarbonate of an alkali metal or ammonium hydroxide, preferably an alkali metal hydroxide, specifically sodium hydroxide, potassium hydroxide and lithium hydroxide. Sodium hydroxide or potassium hydroxide is preferred from the standpoint of commercial availability, price, safety and the like.

The concentration of the aqueous solution containing the acrylic acid type monomers and the optional second monomer is not particularly limited, but is usually 20% by weight or more, preferably 30% by weight or more. It is generally desirable to make the concentration as high as possible. Because the amount of a highly water absorptive polymer applied per unit surface area of a fibrous substrate increases as the monomer concentration increases, leading to production of an enhanced water absorption capacity. Furthermore, a higher monomer concentration means a lower water concentration, which means a reduced energy required for drying and thus a lower production cost.

Crosslinking Agent

The crosslinking agent to be used in the process of the present invention is one which has two or more double bonds in the molecule and is copolymerizable with the acrylic acid type monomer and(or) the second monomer, or one which has two or more functional groups in the molecule that can be reacted with the functional groups in the acrylic acid type monomer and(or) the second monomer during polymerization or upon the subsequent drying. Any compound as mentioned above may be used provided it exhibits water-solubility to some extent.

Examples of the former crosslinking agents may include ethylene glycol di(meth)acrylate, diethylene glycol di(meth)acrylate, polyethylene glycol di(meth)acrylate, propylene glycol di(meth)acrylate, polypropylene glycol di(meth)acrylate, glycerine tri(meth)acrylate, N,N'-methylenebis(meth)acrylamide, diallyl phthalate, diallyl maleate, diallyl terephthalate, triallyl cyanurate, triallyl isocyanurate, triallyl phosphate, trimethylolpropane tri(meth)acrylate, tetramethylolmethane tri(meth)acrylate, dipentaerythritol hexaacrylate.

Examples of the latter crosslinking agents may include ethylene glycol diglycidyl ether, polyethylene glycol diglycidyl ether, di- or polyglycidyl ethers of aliphatic polyvalent alcohols.

Further, these compounds which possess both the functions of the former and the latter such as N-methylolacrylamide and glycidyl methacrylate may also be used in the process according to the present invention.

Among the crosslinking agents mentioned above, those having two or more double bonds in the molecule and copolymerizable with the acrylic acid type monomer and(or) the second monomer are preferred.

The crosslinking agents may be used alone or in a mixture of two or more of them.

The amount of the crosslinking agent used is 0.001 to 10% by weight, preferably 0.01 to 2% by weight based on the acrylic acid type monomer. At a level less than 0.001% by weight, while the water absorption capacity of the resulting polymer may be greater, the gel strength of the polymer swelled with water will become smaller. On the other hand, at a level exceeding 10% by weight, while the gel strength can be remarkably enhanced, the water absorption capacity of the polymer becomes too low for practical use.

Polyoxyethylene Acyl Ester

The polyoxyethylene acyl ester used in the present invention has HLB (hydrophilic-lipophilic balance; measured by the Atlas method) of 7 or more, and is preferably one which can substantially dissolve in the aqueous solution containing the acrylic acid type monomers. The degree of condensation of the ethylene oxide and the number of carbon atoms in the acyl group should desirably be determined from this standpoint. The number of carbon atoms in the acyl group is preferably about 10 to 20 including the carbon atom in the carbonyl group.

The polyoxyethylene acyl ester is preferably prepared by a method involving addition reaction of ethylene oxide to a corresponding carboxylic acid (typically a monocarboxylic acid having such acyl group as described above). It may thus be said at first that a typical or preferred ester is an alcohol ester. The terminal hydroxyl group of the alcohol ester, which group is derived from the ethylene oxide, can be esterified with ease. Therefore, it may also be said that the further esterified product of the ester alcohol, i.e. diester, is also a typical ester according to the present invention. "Polyoxyethylene" may include a small amount of oxypropylene groups.

Examples of such polyoxyethylene acyl esters may include polyethylene glycol monolaurate, polyethylene glycol dilaurate, polyethylene glycol monostearate, polyethylene glycol distearate, polyethylene glycol monooleate, and polyethylene glycol dioleate.

The polyoxyethylene acyl esters may be used singly or in a mixture of two or more of them.

These polyoxyethylene acyl esters are used in the present invention in an amount of 0.001 to 10% by weight, preferably 0.01 to 1% by weight based on the amount of acrylic acid type monomer used. The amount of less than 0.001% by weight will fail to produce the desired effect. The use of the ester in an amount exceeding 10% by weight is disadvantageous since it rather deteriorate the water absorption capacity of the resulting product.

Oxidative Radical Initiator

The oxidative radical initiator to be used in the process of the present invention forms a redox system with a reducing agent, and must be a radical generating agent which exhibits water-solubility to some extent and possesses oxidizability. Examples of such oxidative agents may include (a) peroxides including hydrogen peroxide, persulfates such as ammonium persulfate, potassium persulfate, hydroperoxides such as tert-butyl hydroperoxide and cumene hydroperoxide and (b) }secondary cerium salts, permanganates, chlorites, hypochlorites, and others.

Among these oxidative agents, hydrogen peroxide is particularly preferred.

Other water soluble radicals exhibiting no oxidizability, for example, azo compounds such as 2,2'-azobis(2-amidinopropane) dihydrochloride, which do not form a redox system with a reducing agent, are not used in the present invention.

The amount of these oxidative radical polymerization initiators used may be about 0.01 to 10% by weight, preferably 0.1 to 2% by weight based on the monomer used.

Prefabricated Fibrous Substrate

The prefabricated fibrous substrate to be used in the process according to the present invention may be one formed by loose fabrication of fibers such as a pad, a carded or air-laid web, tissue paper, a woven fabric like cotton gauze, knitted fabric or nonwoven fabric. The term "prefabricated" fibrous substrate herein used means the substrate which has already been processed into the form of web and thus requires no further web-forming operation, though some operations such as cutting, bonding, shaping and the like may be required for incorporating the fibrous substrate into an article.

In general, absorptive fibers including cellulose fibers such as wood pulp, rayon, cotton and the like and/or polyester fibers are preferably used as a main component for the fibrous substrate. Other kinds of fibers such as those of polyethylene, polypropylene, polystyrene, polyamide, polyvinyl alcohol, polyvinyl chloride, polyvinylidene chloride, polyacrylonitrile, polyurea, polyurethane, polyfluoroethylene, polyvinylidene cyanide and the like may be also incorporated into the prefabricated fibrous substrate.

Application Method

The aqueous solution of the acrylic acid type monomer containing a small amount of the crosslinking agent and polyoxyethylene acyl ester is admixed homogeneously with the oxidative radical polymerization initiator, and the resulting mixture is applied to the prefabricated fibrous substrate. Preferably, the solution mixture is applied to form dotted or linear patterns at periodic intervals. These patterns can be used to form a so-called "suction channel" in the water absorptive composite produced by the process of the present invention. If a continuous strip of a crosslinked water absorptive polymer is applied, for example, on the periphery of the water absorptive pad portion in a diaper, leakage of a fluid from the periphery will be notably reduced. Generally, it is desirable that patterns comprising very finely divided discontinuous portions be adopted in order to maximize the ratio of the surface area of the polymer to the mass thereof. The solution mixture can be applied to the fibrous substrate by any means or mode suitable for the purpose, for example, printing, spraying, flowing through a nozzle, kiss coating, and saturating. The solution mixture can be applied in a quantity sufficient to coat only one surface of the fibrous substrate or to cover the thickness thereof.

The solution mixture is maintained at room temperature, more specifically at 20° to 60° C., applied to the fibrous substrate and controlled to have a predetermined temperature, as will be described in detail below, in a reaction vessel.

The solution mixture may further contain other additives than the above mentioned components if desired. The "solution mixture" used herein is basically an aqueous solution, however, if desired, it can be one wherein a small amount of a water-soluble organic solvent is dissolved.

The quantity of the solution mixture to impregnate the fibrous substrate is not particularly limited but can vary over a wide range depending upon the method of use of a water absorptive composite product. In general, from 0.1 to 1,000 parts by weight, ordinarily from 0.5 to 50 parts, of the solution mixture is employed for 1 part by weight of the fibrous substrate.

Step (B)

Reducing Agent

The reducing agent to be used in the process according to the present invention is one which can form a redox system with the above oxidative radical polymerization initiator, and exhibit water solubility to some extent. Specific examples of such reducing agents may include sulfites such as sodium sulfite, sodium hydrogen sulfite, sodium thiosulfate, cobalt acetate, cupric sulfate, ferrous sulfate, L-ascorbic acid and L-ascorbic acid alkali metal salts. Among these, in the present invention, L-ascorbic acid and L-ascorbic acid alkali metal salts are especially preferred.

The amount of these reducing agents used may be 0.001 to 10% by weight, preferably 0.01 to 2% by weight based on the acrylic acid type monomer.

Application of reducing agent and Polymerization Conditions

The solution mixture prepared by homogeneously admixing the aqueous solution of the acrylic acid type monomer containing a small amount of the crosslinking agent and the polyoxyethylene acyl ester with HLB of 7 or more with the oxidative radical polymerization initiator is first applied to the prefabricated fibrous substrate as set forth hereinabove. Subsequently, the reducing agent mentioned above is applied to the fibrous substrate thus coated with the solution mixture at room temperature or, if necessary, after heating to a predetermined temperature to cause a polymerization reaction.

The reducing agent is applied, for example, through a spray nozzle in atomized form whereby a high polymerization reaction efficiency coupled with remarkable operability can be achieved.

In the particular case where the reducing agent is solid at room temperature, it is preferably applied in the form of an aqueous solution.

The temperatures within the reaction vessel and of the reducing agent to be employed are, for example, from room temperature to 60° C., ordinarily from room temperature to 40° C.

The reaction vessel and system are not particularly limited, and those of any type may be applicable. One instance of practice is a method in which a reaction is carried out batchwise in a box-shaped reaction vessel of the oven type or continuously on an endless belt.

The reaction time may vary with the polymerization temperature and the like, but generally from several seconds to about two hours, and preferably from several seconds to about ten minutes.

After completion of the polymerization a crosslinking reaction may be introduced, or the composite may be passed through a series of dryers or placed in a forced draft furnace to remove moisture, if necessary.

EXPERIMENTAL EXAMPLES

The following examples are to illustrate some embodiments of the present invention without implying a limitation. In the examples, saline solution absorption capacity and water absorption rate were determined by the following methods.

A. Saline Solution Absorption Capacity

About 1.0 g of a water absorptive composite and about 200 g of a saline solution having a concentration of 0.9% by weight were precisely weighed, respectively and charged in a 300 ml beaker. The beaker was left standing for about 4 hours to swell the polymer sufficiently with the solution. The beaker content was filtered through a 100-mesh sieve, and the amount of the filtrate was weighed and saline solution absorption capacity was calculated according to the following equation:

$$\text{Saline solution absorption capacity} = \frac{\left(\begin{array}{c}\text{Charged amount of}\\ \text{saline solution (g)}\end{array}\right) - \left(\begin{array}{c}\text{Amount of}\\ \text{filtrate (g)}\end{array}\right)}{\left(\begin{array}{c}\text{Charged amount of water}\\ \text{absorptive composite (g)}\end{array}\right)}$$

B. Water Absorption Rate

About 200 g of a saline solution having a concentration of 0.9% by weight was weighed and charged in a 300 ml beaker. Subsequently, about 1.0 g of a water absorptive composite was weighed and added to the saline solution. After 5 minutes, the beaker content was filtered through a 100-mesh sieve. The amount of the filtrate was weighed and saline solution absorption capacity was calculated according to the equation set forth in A, and the thus calculated value was regarded as water absorption rate.

EXAMPLE 1

In a 100 cc conical flask, 30 g of acrylic acid was placed and 17.0 g of pure water and 0.032 g of polyethylene glycol dilaurate (HLB=14) were added thereto to dissolve the acrylic acid. The mixture was neutralized by slowly adding 18.3 g of potassium hydroxide (about 95% by weight) under ice cooling. The neutralization degree of acrylic acid was about 75%.

0.05 g of N,N'-methylenebisacrylamide as a crosslinking agent was added to and dissolved in the above mentioned monomer solution, and then 0.8 g of 31% aqueous hydrogen peroxide as a radical polymerization initiator was dissolved in the mixture.

3.68 g of a polyester nonwoven fabric was provided, and the whole surface of the nonwoven fabric was coated and impregnated with the aforementioned raw material, and the nonwoven fabric thus treated was maintained at a temperature of 40° C. in a constant temperature bath. The amount of the monomer thus impregnated was 5.9 times the weight of the nonwoven fabric.

Next, an aqueous solution of 5% L-ascorbic acid was sprayed through a spray nozzle onto the whole surface of the above mentioned nonwoven fabric. Polymerization started immediately and a water absorptive composite in which a highly water absorptive polymer was firmly held on the polyester nonwoven fabric was obtained.

The saline solution absorption capacity of the above water absorptive composite was found to be 49.8, and the water absorption rate 39.5.

EXAMPLE 2

In a 100 cc conical flask, 13.1 g of sodium hydroxide (purity: about 95% by weight) was placed and dissolved in 39.0 g of pure water under ice cooling. The aqueous solution was neutralized by slowly adding 30 g of acrylic acid under ice cooling. The neutralization degree of acrylic acid was about 75%.

0.032 g of polyethylene glycol dilaurate, 0.05 g of N,N'-methylenebisacrylamide as a crosslinking agent and 0.8 g of 31% aqueous hydrogen peroxide as a radical polymerization initiator were added and dissolved in the aqueous solution.

Separately, 3.59 g of a polyester nonwoven fabric was provided, and the whole surface of the nonwoven fabric was coated and impregnated with the above mentioned raw material, and the coated nonwoven fabric was maintained at a temperature of about 40° C. in a constant temperature bath. The amount of the monomer thus impregnated was 4.6 times the weight of the nonwoven fabric.

Next, an aqueous solution of 5% L-ascorbic acid as a reducing agent was sprayed through a spray nozzle onto the whole surface of the above mentioned nonwoven fabric. Polymerization started immediately and a water absorptive composite in which a highly water absorptive polymer was firmly held on the polyester nonwoven fabric was obtained.

The saline solution absorption capacity of the above water absorptive composite was found to be 47.9, and the water absorption rate 41.5.

EXAMPLE 3

In a 100 cc conical flask, 26.9 g of 25% aqueous ammonia was placed and neutralized by slowly adding 30 g of acrylic acid under ice cooling. The neutralization degree of acrylic acid was about 95%.

0.032 g of polyethylene glycol dilaurate, 0.05 g of N,N'-methylenebisacrylamide as a crosslinking agent and 0.8 g of 31% aqueous hydrogen peroxide as a polymerization initiator were added and dissolved in the above aqueous solution.

Separately, 2.59 g of a polyester nonwoven fabric was provided, and the whole surface of the nonwoven fabric was coated and impregnated with the above mentioned raw material, and the coated nonwoven fabric was maintained at a temperature of about 40° C. in a constant temperature bath. The amount of the monomer thus impregnated was 6.5 times the weight of the nonwoven fabric.

Next, an aqueous solution of 5% L-ascorbic acid as a reducing agent was sprayed through a spray nozzle onto the whole surface of the above mentioned nonwoven fabric. Polymerization started immediately and a water absorptive composite in which a highly water absorptive polymer was firmly held on the polyester nonwoven fabric was obtained.

The saline solution absorption capacity of the above water absorptive composite was found to be 43.2, and the water absorption rate 35.5.

EXAMPLE 4

A water absorptive composite was prepared in the same way as in Example 1 except for using a rayon nonwoven fabric and changing the amount of the monomer impregnated to 4.5 times the weight of the nonwoven fabric.

The saline solution absorption capacity of the above water absorptive composite was found to be 49.5, and the water absorption rate 40.5.

EXAMPLE 5

A water absorptive composite was prepared in the same way as in Example 1 except for changing the amount of pure water to be added to acrylic acid to 18.7 g and the amount of potassium hydroxide to 14.7 g (thereby changing the neutralization degree of acrylic acid to about 60%).

The saline solution absorption capacity of the above water absorptive composite was found to be 50.5, and the water absorption rate 41.2.

EXAMPLE 6

A water absorptive composite was prepared in the same way as in Example 2 except for using 0.2 g of potassium persulfate as a radical polymerization initiator and changing the reducing agent to 5% aqueous solution of sodium bisulfite.

The saline solution absorption capacity of the above water absorptive composite was found to be 42.5, and the water absorption rate 38.1.

EXAMPLE 7

A water absorptive composite was prepared in the same way as in Example 1 except for using 0.1 g of polyethylene glycol (PEG600) diacrylate as a crosslinking agent.

The saline solution absorption capacity of the above water absorptive composite was found to be 58.1, and the water absorption rate 41.5.

EXAMPLE 8

A water absorptive composite was prepared in the same manner as in Example 2 except for using 0.095 g of polyethylene glycol dioleate (HLB=10) in place of 0.032 g of polyethylene glycol dilaurate (HLB=14).

The saline solution absorption capacity of the above water absorptive composite was found to be 48.6, and the water absorption rate 35.5.

EXAMPLE 9

A water absorptive composite was prepared in the same way as in Example 1 except for using 0.095 g of polyethylene glycol dioleate (HLB=10) in place of 0.032 g of polyethylene glycol dilaurate (HLB=14).

The saline solution absorption capacity of the above water absorptive composite was found to be 47.2, and the water absorption rate 34.3.

EXAMPLE 10

A water absorptive composite was prepared in the same way as in Example 1 except that application of the monomer solution to the surface of the polyester nonwoven fabric was carried out in such a manner that the monomer solution was sprayed through a spray nozzle so that the solution would make small spots on the fabric and that the amount of the monomer thus impregnated was changed to 4.5 times the weight of the nonwoven fabric.

The saline solution absorption capacity of the above water absorptive composite was found to be 50.5, and the water absorption rate 42.1.

The water absorptive composite bore finely divided highly water absorptive polymer firmly fixed to the fabric and had a very soft touch to afford a good utility for sanitary goods such as a sanitary napkin and a paper diaper.

EXAMPLE 11

A water absorptive composite was prepared in the same way as in Example 1 except that application of the monomer solution to the surface of the polyester nonwoven fabric was carried out in such a manner that the monomer solution was coated on and impregnated into the fabric using a role coater so that the solution applied would form a pattern of continuous stripes along the fibers and that the amount of the monomer thus impregnated was changed to 6.3 times the weight of the nonwoven fabric.

The saline solution absorption capacity of the above water absorptive composite was found to be 51.2, and the water absorption rate 48.8.

The water absorptive composite bore highly water absorptive polymer firmly fixed to the composite in a pattern of continuous stripes along the fibers of the nonwoven fabric and had a high water absorption rate to afford a good utility not only for sanitary goods such as a sanitary napkin and a paper diaper but also for a water retaining agent for agriculture.

COMPARATIVE EXAMPLE 1

A water absorptive composite was prepared in the same way as in Example 1 except for not using polyethylene glycol dilaurate.

The saline solution absorption capacity of the composite was found to be 48.5, and the water absorption rate 15.6.

COMPARATIVE EXAMPLE 2

A water absorptive composite was prepared in the same way as in Example 2 except for not using polyethylene glycol dilaurate.

The saline solution absorption capacity of the composite was found to be 45.8, and the water absorption rate 12.2.

COMPARATIVE EXAMPLE 3

A water absorptive composite was prepared in the same way as in Example 3 except for not using polyethylene glycol dilaurate.

The saline solution absorption capacity of the composite was found to be 41.2, and the water absorption rate 12.3.

COMPARATIVE EXAMPLE 4

A water absorptive composite was prepared in the same way as in Example 5 except for not using polyethylene glycol dilaurate.

The saline solution absorption capacity of the composite was found to be 48.6, and the water absorption rate 15.3.

COMPARATIVE EXAMPLE 5

An aqueous solution of partially neutralized potassium acrylate of a neutralization degree of 75% having the monomer concentration of about 65% by weight was prepared. This aqueous solution was coated on and impregnated into the whole surface of a polyester nonwoven fabric. The amount of the monomer thus impregnated was about ten times the weight of the nonwoven fabric.

The nonwoven fabric having been impregnated with the aqueous solution of the partially neutralized potassium acrylate monomer was irradiated with electron beam at a dose of 10 Mrad by means of an electron beam generating apparatus equipped with a DYNAMITRON accelerator. Polymerization started immediately and a water absorptive composite in which a highly water absorptive polymer comprising a partially neutralized self-crosslinked potassium polyacrylate was firmly held on the polyester nonwoven fabric was obtained.

The saline solution absorption capacity of the water absorptive composite was found to be 18.5, and the water absorption rate 15.5.

COMPARATIVE EXAMPLE 6

An aqueous solution of partially neutralized sodium acrylate of a neutralization degree of 75% having the monomer concentration of about 45% by weight was prepared. This aqueous solution was coated on and impregnated into the whole surface of a polyester nonwoven fabric. The amount of the monomer thus impregnated was about 13 times the weight of the nonwoven fabric.

The nonwoven fabric having been impregnated with the aqueous solution of the partially neutralized sodium acrylate monomer was irradiated with electron beam at a dose of 10 Mrad by means of an electron beam generating apparatus equipped with a DYNAMITRON accelerator. Polymerization started immediately and a water absorptive composite in which a highly water absorptive polymer comprising a partially neutralized self-crosslinked sodium polyacrylate was firmly held on the polyester nonwoven fabric was obtained.

The water absorptive composite thus obtained was found to contain almost no residual monomers, and have the saline solution absorption capacity of 25.0 and the water absorption rate of 18.9.

COMPARATIVE EXAMPLE 7

An aqueous solution of partially neutralized sodium acrylate of a neutralization degree of 75% having the monomer concentration of about 45% by weight was prepared. To this solution was added 0.0085 g of N,N'-methylenebisacrylamide as a crosslinking agent to dissolve the same. This monomer solution was coated on and impregnated into a polyester nonwoven fabric, and the temperature of the nonwoven fabric was adjusted to 70° C. The amount of the monomer impregnated was 11 times the weight of the nonwoven fabric. When a 16.7% aqueous solution of 2,2'-azobis(2-amidinopropane) dihydrochloride was sprayed through a spray nozzle onto the nonwoven fabric, polymerization started immediately. However, polymerization took place only in the upper portion of the nonwoven fabric and the water absorptive composite obtained had a strong odor of monomers (the amount of residual monomers was about 15% by weight). The above aqueous solution containing the polymerization initiator was further sprayed onto the water absorptive composite at 70° C., and the composite was maintained at the temperature for 30 minutes, but polymerization hardly proceeded. Then the resulting water absorptive composite was dried under vacuum at 90° C. and the saline solution absorption capacity and the water absorption rate thereof were measured, which were found to be as low as 16.5 and 2.3, respectively.

COMPARATIVE EXAMPLE 8

An aqueous solution of partially neutralized potassium acrylate of a neutralization degree of 75% having the monomer concentration of about 65% by weight was prepared. To this solution was added 0.010 g of N,N'-methylenebisacrylamide as a crosslinking agent to dissolve the same. This monomer solution was coated on and impregnated into a polyester nonwoven fabric, and the temperature of the nonwoven fabric was adjusted to 70° C. The amount of the monomer impregnated was 10 times the weight of the nonwoven fabric. When a 16.7 % aqueous solution of 2,2'-azobis(2-amidinopropane) dihydrochloride was sprayed through a spray nozzle onto the nonwoven fabric, polymerization started immediately. However, similarly as in Comparative Example 7, polymerization took place only in the upper portion of the nonwoven fabric and the water absorptive composite obtained had a strong odor of monomers (the amount of residual monomers was about 12.1% by weight).

Then the water absorptive composite was maintained at 90° C. for 30 minutes, and dried under vacuum at the same temperature. The saline solution absorption capacity of the composite was found to be as low as 14.2, and the water absorption rate 5.3.

What is claimed is:

1. A process for preparing a water absorptive composite, which comprises the combination of the steps of:
   (A) applying an aqueous solution containing (a) 20% by weight or more of a polymerizable monomer consisting as a main component acrylic acid, of which 20% or more of the carboxyl groups have been neutralized to its alkali metal salt or ammonium salt, (b) 0.001 to 10% by weight based on the polymerizable monomer (a) of a crosslinking agent, (c) 0.001 to 10% by weight based on the polymerizable monomer (a) of a polyoxyethylene acyl ester with HLB of 7 or more and (d) 0.01 to 10% by weight based on the polymerizable monomer (a) of an oxidative radical polymerization initiator to a prefabricated fibrous substrate and
   (B) polymerizing the polymerizable monomer applied to said fibrous substrate with addition of a reducing agent to form a composite of a polymer derived from said polymerizable monomer and said fibrous substrate.

2. The process according to claim 1, wherein the polymerization is carried out for several seconds to ten minutes.

3. The process according to claim 1, wherein said amount is 0.01 to 1 mol %.

4. The process according to claim 1, wherein the polyoxyethylene acyl ester (c) is selected from the group consisting of polyethylene glycol monolaurate, polyethylene glycol dilaurate, polyethylene glycol monostearate, polyethylene glycol distearate, polyethylene glycol mono-oleate, and polyethylene glycol di-oleate.

5. The process according to claim 1, wherein the aqueous solution further contains an additional monomer selected from the group consisting of (a) methacrylic acid, itaconic acid, maleic acid, fumaric acid, 2-acrylamide-2-methylpropanesulfonic acid, 2-acryloylethanesulfonic acid, 2-acryloylpropanesulfonic acid and the salts thereof, (b) 2-vinylpyridine, 4-vinylpyridine and the salts thereof, (c) an alkyl or alkoxy ester of a dicarboxylic acid selected from itaconic acid, maleic acid and fumaric acid, (d) vinylsulfonic acid, (e) methyl acrylate and ethyl acrylate, (f) hydroxyethyl (meth)acrylate and hydroxypropyl (meth)acrylate and (g) polyethylene glycol mono(meth)acrylate.

6. The process according to claim 1, wherein the acrylic monomer (a) is one which has been neutralized with sodium hydroxide or patassium hydroxide.

7. A water absorptive composite produced by the process according to claim 1.

8. The process according to claim 1, wherein the crosslinking agent (b) is one which has two or more double bonds in the molecule and is copolymerizable with the acrylic monomer (a).

9. The process according to claim 1, wherein the oxidative radical polymerization initiator (d) and the reducing agent are those which can form a redox system therebetween.

10. The process according to claim 9, wherein the oxidative radical polymerization initiator (d) is selected from the group consisting of (a) a peroxide selected from hydrogen peroxide, persulfates and hydroperoxides and (b) secondary cerium salts, permanganates, chlorites, and hypochlorites.

11. The process according to claim 9, wherein the reducing agent is selected from the group consisting of sulfites, sodium thiosulfate, cobalt acetate, cupric sulfate, ferrous sulfate, L-ascorbic acid and L-ascorbic acid alkali metal salts.

12. The process according to claim 9, wherein the oxidative radical polymerization initiator is hydrogen peroxide and the reducing agent is L-ascorbic acid or its alkali metal salt.

13. The process according to claim 1, wherein the fibrous substrate is a pad of loose fabric, a carded web, an air-laid web, a paper, a nonwoven fabric, a woven fabric or a knitted fabric.

14. The process according to claim 1, wherein the fibrous substrate comprises as a main component cellulose fibers or polyester fibers.

15. The process according to claim 1, wherein the aqueous solution is applied to form dotted or linear patterns at periodic intervals on the fibrous substrate.

16. The process according to claim 1, wherein the reducing agent is applied through a spray nozzle in atomized form.

17. The process according to claim 1, wherein the temperature of the aqueous solution is maintained at 20° to 60° C. while it is being applied to the fibrous substrate.

18. The process according to claim 1, wherein the polymerization is carried out at room temperature to 60° C.

19. The process according to claim 18, wherein the polymerization temperature is from room temperature to 40° C.

* * * * *